(12) United States Patent
Soon-Shiong et al.

(10) Patent No.: US 11,221,328 B2
(45) Date of Patent: Jan. 11, 2022

(54) HYPOXIC NK CELLS AND METHODS THEREFOR

(71) Applicant: NANTCELL, INC., Culver City, CA (US)

(72) Inventors: Patrick Soon-Shiong, Culver City, CA (US); Shahrooz Rabizadeh, Culver City, CA (US); Kayvan Niazi, Culver City, CA (US); Stephen Charles Benz, Culver City, CA (US); Laurent H. Boissel, Culver City, CA (US); Hans Klingemann, Culver City, CA (US); Barry J. Simon, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

(21) Appl. No.: 16/491,559

(22) PCT Filed: Mar. 7, 2018

(86) PCT No.: PCT/US2018/021303
§ 371 (c)(1),
(2) Date: Sep. 5, 2019

(87) PCT Pub. No.: WO2018/165265
PCT Pub. Date: Sep. 13, 2018

(65) Prior Publication Data
US 2020/0041490 A1 Feb. 6, 2020

Related U.S. Application Data

(60) Provisional application No. 62/468,863, filed on Mar. 8, 2017.

(51) Int. Cl.
*C12Q 1/6886* (2018.01)
*G01N 33/50* (2006.01)
*G16H 50/30* (2018.01)
*C12N 5/0783* (2010.01)

(52) U.S. Cl.
CPC ....... *G01N 33/5047* (2013.01); *C12N 5/0646* (2013.01); *C12Q 1/6886* (2013.01); *G16H 50/30* (2018.01); *C12Q 2600/158* (2013.01); *G01N 2800/7014* (2013.01); *G01N 2800/7038* (2013.01)

(58) Field of Classification Search
None
See application file for complete search history.

(56) References Cited

U.S. PATENT DOCUMENTS

2003/0044862 A1   3/2003 Giaccia et al.

FOREIGN PATENT DOCUMENTS

| CA | 3 055 958 A1 | 9/2018 |
|---|---|---|
| CN | 110891581 A | 3/2020 |
| JP | 2020-509750 A | 4/2020 |
| KR | 10-2019-0126369 A | 11/2019 |
| WO | 2013040371 A2 | 3/2013 |
| WO | 2015/121295 A1 | 8/2015 |
| WO | 2017188790 A1 | 11/2017 |
| WO | 2018/165265 A1 | 9/2018 |

OTHER PUBLICATIONS

Enard et al. (Science 2002 vol. 296 p. 340) (Year: 2002).*
Bakker et al. Molecular Cell vol. 28 2007 p. 941-953) (Year: 2007).*
Notice of Acceptance received for Australian Patent Application Serial No. 2018230346 dated Oct. 2, 2020, 3 pages.
Office Action received for Canadian patent Application Serial No. 3055958 dated Aug. 27, 2020, 5 pages.
Notification of Reason for Refusal received for Korean Patent Application Serial No. 10-2019-7029335 dated Sep. 26, 2020, 13 pages (Including English translation).
Allen et al., "Gene expression, methylation and neuropathology correlations at progressive supranuclear palsy risk loci", Acta Neuropathol, 2016, vol. 132, No. 2, 25 pages.
Second Examination Report received in Australian Patent Application Serial No. 2018230346 dated Aug. 12, 2020, 3 pages.
Balsamo et al., "Hypoxia downregulates the expression of activating receptors involved in NK-cell-mediated target cell killing without affecting ADCC",Eur. J. Immunol., 2013, vol. 43, pp. 2756-2764, DOI: 10.1002/eji.201343448.
Fionda et al., "Inhibition of glycogen synthase kinase-3 increases NKG2D ligand MICA expression and sensitivity to NK cell-mediated cytotoxicity in multiple myeloma cells: role of STAT3" The Journal of Immunology, May 17, 2013, vol. 190, No. 12, pp. 6662-6672.
Jochems et al., "An NK cell line (haNK) expressing high levels of granzyme and engineered to express the high affinity CD16 allele" Oncotarget, 2016, Nov. 16, 2016, vol. 7, No. 52, pp. 86359-86373.
Krzywinska et al., "Loss of HIF-1a in natural killer cells inhibits tumour growth by stimulating non-productive angiogenesis," Nature Communications, Nov. 17, 2017, vol. 8, No. 1, pp. 13, DOI: 10.1038/s41467-017-01599-w.
Lavecchia et al., "STAT-3 inhibitors: state of the art and new horizons for cancer treatment," Current Medicinal Chemistry, Jun. 1, 2011 ,vol. 18, No. 1, pp. 17.

(Continued)

*Primary Examiner* — Katherine D Salmon
(74) *Attorney, Agent, or Firm* — Martin Fessenmaier; Umberg Zipser LLP

(57) ABSTRACT

Detection of under-expression of selected genes in NK cells is used to confirm a hypoxic tumor microenvironment that is ordinarily suppressive with respect to ADCC and cytotoxic cell killing of NK cells. Most notably, while hypoxia is known to upregulate HIF-1α and genes under the control of HIF-1α, hypoxia in a tumor microenvironment led to under-expression of selected genes, including HIF-1α. Thus, gene expression analysis of certain genes on NK cells can be used to detect conditions in a tumor that would indicate use of haNK cells.

4 Claims, 7 Drawing Sheets

(56) References Cited

OTHER PUBLICATIONS

Murray et al., "Targeting the tumor microenvironment to improve natural killer cell-based immunotherapies: On being in the right place at the right time, with resilience", Human Vaccines & Immunotherapeutics, 2016, vol. 12, No. 3, pp. 607-611.
Noman et al., "The cooperative induction of hypoxia-inducible factor ! alpha and ST A T3 during hypoxia induced an impairment of tumor susceptibility to CTL-mediated cell lysis", The Journal of Immunology, 2009, vol. 182, pp. 3510-3521, DOI: 10.4049/jimmunol. 0800854.
Velasquez et al., "Short Term Hypoxia Synergizes with Interleukin 15 Priming in Driving Glycolytic Gene Transcription and Supports Human Natural Killer Cell Activities", The Journal of Biological Chemistry, Jun. 17, 2016, vol. 291, No. 25, pp. 12960-12977.
International Preliminary Report on Patentability for PCT Application No. PCT/US2018/016513, dated Aug. 29, 2019 pp. 15.
First Examination Report received in Australian Patent Application Serial No. 2018230346 dated Jul. 16, 2020, 9 pages.
International Preliminary Report On Patentability received for PCT Application Serial No. PCT/US2018/021303 dated Jul. 11, 2019, 16 pages.
Gotthardt et al., "Loss of STAT3 in murine NK cells enhances NK cell-dependent tumor surveillance", Blood, 2014, vol. 124, No. 15, pp. 2370-2379.
Ghadially et al., "MHC class I chain-related protein A and B (MICA and MICB) are predominantly expressed intracellularly in tumour and normal tissue", British Journal of Cancer, 2017, vol. 116, pp. 1208-1217.
Mckeown S R, "Defining normoxia, physoxia and hypoxia in tumours-implications for treatment response", British Institute of Radiology, 2014, 12 pages.
Schilling et al., "A hypoxia-induced decrease of either MICA/B or Hsp70 on the membrane of tumor cells mediates immune escape from NK cells", Cell Stress and Chaperones, 2015, vol. 20, pp. 139-147.
Yue et al., "Targeting STAT3 in cancer: how successful are we?", Expert Opin Investig Drugs, 2009, vol. 18, No. 1, 18 pages.
Hasmim et al., "Critical role of tumormicroenvironment in shaping NK cellfunctions: implication of hypoxicstress", Frontiers in Immunology, 2015, vol. 6, No. 482, pp. 1-9.
Zhang et al., "Interleukin-12 improves cytotoxicity of natural killer cells via upregulated expression of NKG2D", Human Immunology, 2008, vol. 69, No. 8, pp. 490-500.
Yamada et al., "Hypoxia downregulates the expression of cell surface MICA without increasing soluble MICA in osteosarcoma cells in a HIF-1α-dependent manner", International Journal of Oncology, 2012, vol. 41, pp. 2005-2012.
Hockel et al., "Tumor Hypoxia: Definitions and Current Clinical,Biologic, and Molecular Aspects", Journal of the National Cancer Institute, 2001, vol. 93, No. 4, pp. 266-276.
Hu et al., "CD8+T cell-specific induction of NKG2D receptor by doxorubicin plus interleukin-12 and its contribution to CD8+T cell accumulation in tumors", Molecular Cancer, 2014, vol. 13, No. 34, pp. 1-13.
Codo et al., "MicroRNA-mediated down-regulation of NKG2D ligandscontributes to glioma immune escape", Oncotarget, vol. 5 No. 17, pp. 7651-7662.
Hochheiser et al., "CRISPR/Cas9: A tool for immunological research", European Journal of Immunology, 2018, vol. 48, pp. 576-583.
International Search Report received for PCT Application Serial No. PCT/US2018/021303 dated Jun. 19, 2018, 14 pages.
Solocinski et al., "Overcoming hypoxia-induced functional suppression of NK cells", Journal of ImmunoTherapy of cancer, 2020, vol. 8, pp. 1-12.
Bruhns et al., "Specificity and affinity of human Fcγ receptors and their polymorphic variants for human IgG subclasses", Blood, 2009, vol. 113, No. 16, pp. 3716-3725.
Groot et al., "Modulation of antiangiogenic resistance: Targeting the JAK/STAT3 pathway", 2012, vol. 30, No. 15, 25-29, 32-35.
Third Examination Report received in Australian Patent Application Serial No. 2018230346 dated Aug. 25, 2020, 3 pages.
Notice of Reasons for Refusal received in Japanese Patent Application Serial No. 2019-548749 dated Aug. 4, 2020, 9 pages (Including English Translation).
Sarkar et al., "Hypoxia Induced Impairment of NK Cell Cytotoxicity against Multiple Myeloma Can Be Overcome by IL-2 Activation of the NK Cells", Plos One, 2013, vol. 5, No. 8, e64835, pp. 1-12.
Tanaka Toshiyaki, "Cell Trafficking via Blood and Lymphatic Vessel and Immune Surveillance", Laboratory of Immunobiology,2008, pp. 1-8.
Berchem et al., "Hypoxic tumor-derived microvesicles negatively regulate NK cell function by a mechanism involving TGF-beta and miR23a transfer", OncoImmunology, Apr. 8, 2016, vol. 5, No. 4,p. e1062968, 36 pages.
Groot et al., "Modulating Antiangiogenic Resistance by Inhibiting the Signal Transducer and Activator of Transcription 3 Pathway in Glioblastoma", Oncotarget, Sep. 19, 2012, vol. 3, No. 9, pp. 1036-1048.
Extended European Search Report received for European Patent Application Serial No. 18764366.3 dated Mar. 1, 2021, 12 pages.
Notice of Final Rejection received for Korean Patent Application Serial No. 10-2019-7029335 dated Mar. 26, 2021, 15 pages (Including English Translation).
Decision of Refusal received for Japanese Patent Application Serial No. 2019548749 dated May 7, 2021, 8 pages (Including English Translation).
Notification of Reason for Refusal received for Korean Patent Application Serial No. 1020197029335 dated Jun. 27, 2021, 22 pages (Including English Translation).
GenBank "*Homo sapiens* pyrin and HIN domain family member 1 (PYHIN1), RefSeqGene on chromosome 1", NCBI Reference Sequence: NG_029756.1, 2016, 12 pages.
Communication pursuant to Rule 164(1) EPC received for European Patent Application Serial No. 18764366.3 dated Nov. 27, 2020, 14 pages.
Office Action received for Canadian Patent Application Serial No. 3055958 dated Oct. 22, 2021, 6 pages.
McCann et al., "Targeting constitutively-activated STAT3 in hypoxic ovarian cancer, using a novel STAT3 inhibitor", Oncoscience, 2014, vol. 1, No. 3, pp. 216-228.

* cited by examiner

HYPOXIC NK CELLS AND METHODS THEREFOR

This application claims priority to US provisional application with the Ser. No. 62/468,863, which was filed Mar. 8, 2017.

FIELD OF THE INVENTION

The field of the invention is various compositions and methods relating to natural killer (NK) cells, especially as it relates to NK cells that retain activity under hypoxic conditions in a tumor microenvironment.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Immune therapy of cancer has recently gained significant attention, due to favorable treatment outcomes in at least some cases. However, it has also become apparent that the tumor microenvironment can undergo certain changes that result in immune evasion. Among other known mechanisms, escape from immune surveillance may be mediated by secretion of immune suppressive cytokines, secretion of one or more soluble immune checkpoint and/or NKG2D ligands, chemokine-based attraction of suppressor cells, and epithelial-mesenchymal transition. These factors are also in interplay with metabolic deprivation and hypoxia, which has been shown to render NK cells significantly less active in the tumor microenvironment. For example, hypoxia was shown to downregulate the expression of activating receptors involved in NK-cell-mediated target cell killing (see e.g., *Eur. J. Immunol.* 2013. 43: 2756-2764). Additionally, hypoxia was also demonstrated to downregulate NKG2D ligands on tumor cells (see e.g., *Cell Stress and Chaperones* (2015) 20:139-147), and to significantly impair or even block NK cell mediated cytotoxicity (see e.g., *Front Immunol* 2015, 6:482) in a variety of possible direct and indirect mechanisms.

To improve cytotoxicity, various attempts have been undertaken. For example, IL-12 was shown in vitro to enhance cytotoxicity of NK cells to different solid and hematological tumor cell lines and to promote interferon-gamma secretion by NK cells (see e.g., *Hum Immunol.* 2008 August; 69(8):490-500). However, the IL-12 concentrations used in vitro may not necessarily reflect achievable or even desirable levels in vivo. Similarly, doxorubicin plus IL-12 was shown in vitro to specifically increase expression of NKG2D in CD8+T cells but not in other types of immune cells, including NK cells, which naturally express NKG2D (see e.g., *Molecular Cancer* 2014 13:34). While at least somewhat effective in vivo for CD8+ T cells, no significant effect was shown for NK cells. Hypoxia induced impairment of NK cell cytotoxicity against multiple myeloma can be overcome by IL2 activation of the NK cells (see e.g., *PLoS ONE* 8(5): e64835). Unfortunately, IL2 is systemically not well tolerated at doses required to reactivate NK cells. To still further compound difficulties associated with a hypoxic tumor microenvironment, there is no reliable method to identify hypoxia in a tumor.

Therefore, there remains a need for compositions and methods to identify hypoxia and attendant reduction of NK cell activity in a tumor microenvironment, and for methods to take advantage of hypoxia resistant NK cells in such a microenvironment.

SUMMARY OF THE INVENTION

The inventive subject matter is directed to various methods of detecting and treating a patient having a hypoxic tumor microenvironment. Most preferably, hypoxia is detected via detection of under-expression of selected genes in NK cells. Unexpectedly, and contrary to common knowledge, hypoxia in a tumor microenvironment was associated with a decreased expression of HIF-1α and genes regulated by HIF-1α in NK cells. Thus, where hypoxia in a tumor microenvironment is detected, appropriate countermeasures can be taken, such as administration of allogenic recombinant NK cells having significantly reduced sensitivity to hypoxic conditions, or administration of a drug that restores normal expression levels in the affected NK cells. Alternatively, or additionally, a tumor may also be driven into a hypoxic state (e.g., using bevacizumab), and then be treated with allogenic recombinant NK cells or NK cells that otherwise have significantly reduced sensitivity to hypoxic conditions.

For example, in one aspect of the inventive subject matter, the inventors contemplate a method of a method of testing NK cells of a patient diagnosed with a tumor that includes a step of obtaining blood from the patient, and isolating NK cells from the blood of the patient (e.g., using magnetic separation and an antibody specific to NK cells). In a further step, the expression of at least one hypoxia-related gene in the NK cells is quantified (e.g., using quantitative rtPCR or RNAseq), and under-expression of the hypoxia-related gene is identified relative to an expression level of the hypoxia-related gene in an NK cell at normoxic conditions.

In especially contemplated aspects the hypoxia-related gene is HIF-1α, or a hypoxia-related gene selected from the group consisting of ARL17B, PYHIN1, RPS24, CD52, RPL34, HSPA8, SLIRP, RPS11, B2M, RPS27, MYL12B, RPL39, RPS3A, PTPRC, NAMPT, CALM2, RGS1, KLRB1USP16, RAB8B, RPL26, RPS15A, CCL2, IFI16, CLEC2B, TANK, HSP90AA1, RPS21, KLRK1, RPS29CXCL8, YPEL5, EVI2B, GLIPR1, MARCH7, KLRF1, EIF3E, COX7B, SEC61G, NACA, SAMSN1, USMG5, PSMA4, GAPT, CXCL10, RPL21, MTRNR2L8, MTRNR2L2, MTRNR2L9, and MIR2861, or a hypoxia-related gene selected from the group consisting of GZMA, LAMP1, GZMH, PRF1, BAMB, HIF1A, FCGR3A, KLRK1, GZMK, and GZMM. While not limiting to the inventive subject matter, the hypoxia-related gene is typically under-expressed by a $\log_2$-fold change of at least 1.5, at least 1.7, or at least 2.0. Where desirable, contemplated methods may also include (after the step of identifying under-expression of the at least one hypoxia-related gene), a step of administering at least one of (1) a conditioned NK cell that has reduced inhibition of cell killing in hypoxic conditions as compared to the same NK cell without conditioning; (2) allogenic haNK cells; and (3) a STAT3 inhibitor.

Therefore, the inventors also contemplate a method of diagnosing and treating a tumor having a hypoxic tumor microenvironment. Such methods will generally include a step of obtaining a blood sample from a patient, and isolating NK cells from the blood sample of the patient; and a further step of detecting under-expression of at least one hypoxia-related gene in the isolated NK cells; another step of diagnosing the patient as having a tumor with a hypoxic tumor microenvironment when under-expression of the at least one hypoxia-related gene is detected; and yet a further step of administering an effective amount of allogenic haNK cells (e.g., modified NK92 cells expressing a high affinity variant of CD16) to the diagnosed patient. With respect to the NK cell isolation, quantification of expression, and the hypoxia-related gene, the same considerations as noted above apply.

In another example, the inventors contemplate a method of treating a tumor having a hypoxic tumor microenvironment will include a step of obtaining a blood sample from a patient, and isolating NK cells from the blood sample of the patient; a step of detecting under-expression of at least one hypoxia-related gene in the isolated NK cells; a further step of diagnosing the patient as having a tumor with a hypoxic tumor microenvironment when under-expression of the at least one hypoxia-related gene is detected; and a still further step of administering an effective amount of a STAT3 inhibitor (e.g., an SH2 domain binding inhibitor, a dimerization inhibitor, and/or a DNA binding domain inhibitor) to the diagnosed patient. Once more, with respect to the NK cell isolation, quantification of expression, and the hypoxia-related gene, the same considerations as noted above apply.

Consequently, the inventors also contemplate a method of treating a tumor that includes a step of administering to a patient a drug that reduces tumor neovascularization, wherein the drug is administered in an amount and under a schedule effective to generate a hypoxic tumor microenvironment; and a further step of administering, upon determination of presence of the hypoxic tumor microenvironment, at least one of (1) a conditioned NK cell that has reduced inhibition of cell killing in hypoxic conditions as compared to the same NK cell without conditioning; (2) allogenic haNK cells; and (3) a STAT3 inhibitor.

Most typically, the drug that reduces tumor neovascularization is a drug that blocks VEGF signaling, a drug that inhibits cell proliferation and cell migration of endothelial cells, a drug that down-regulates angiogenesis stimulators and inhibits cell migration of endothelial cells, a drug that inhibits binding of angiogenesis stimulators, and/or a drug that induces apoptosis of endothelial cells. For example, a particularly preferred drug that reduces tumor neovascularization is bevacizumab. It is also preferred that presence of the hypoxic tumor microenvironment is determined using quantitating an expression level of at least one hypoxia-related gene. Especially preferred hypoxia-related genes include ARL17B, PYHIN1, RPS24, CD52, RPL34, HSPA8, SLIRP, RPS11, B2M, RPS27, MYL12B, RPL39, RPS3A, PTPRC, NAMPT, CALM2, RGS1, KLRB1USP16, RAB8B, RPL26, RPS15A, CCL2, IFI16, CLEC2B, TANK, HSP90AA1, RPS21, KLRK1, RPS29CXCL8, YPEL5, EVI2B, GLIPR1, MARCH7, KLRF1, EIF3E, COX7B, SEC61G, NACA, SAMSN1, USMG5, PSMA4, GAPT, CXCL10, RPL21, MTRNR2L8, MTRNR2L2, MTRNR2L9, MIR2861, GZMA, LAMP1, GZMH, PRF1, BAMB, FCGR3A, KLRK1, GZMK, and GZMM.

It is contemplated that the conditioned NK cell is an NK cell that is conditioned with IL-2, or that the allogenic haNK cells are modified NK92 cells expressing a high affinity variant of CD16. Suitable STAT3 inhibitors include SH2 domain binding inhibitors, dimerization inhibitors, and DNA binding domain inhibitors. Where appropriate, a chemotherapeutic drug may be administered or the tumor may be irradiated (e.g., under a schedule and dosage effective to increase expression of an NKG2D ligand on the tumor cells, and/or using low dose administration or low dose irradiation, optionally in a metronomic fashion).

Therefore, the inventors also contemplate in yet another example a method of treating a tumor that includes a step of administering to a patient a drug that reduces tumor neovascularization, wherein the drug is administered in an amount and under a schedule effective to generate a hypoxic tumor microenvironment; a step of obtaining a blood sample from a patient, and isolating NK cells from the blood sample of the patient; and a further step of detecting under-expression of at least one hypoxia-related gene in the isolated NK cells. The tumor is then diagnosed as having the hypoxic tumor microenvironment when under-expression of the at least one hypoxia-related gene is detected, and in another step, an effective amount of allogenic haNK cells are administered upon diagnosis. With respect to the drug, and the hypoxia-related gene, the same considerations as noted above apply.

Therefore, use of at least one hypoxia-related gene is contemplated in a method for in vitro diagnosis of hypoxia in a tumor microenvironment, wherein the method includes a step of quantification of gene expression of the hypoxia-related gene in an isolated NK cell. As before, preferred hypoxia-related genes include ARL17B, PYHIN1, RPS24, CD52, RPL34, HSPA8, SLIRP, RPS11, B2M, RPS27, MYL12B, RPL39, RPS3A, PTPRC, NAMPT, CALM2, RGS1, KLRB1USP16, RAB8B, RPL26, RPS15A, CCL2, IFI16, CLEC2B, TANK, HSP90AA1, RPS21, KLRK1, RPS29CXCL8, YPEL5, EVI2B, GLIPR1, MARCH7, KLRF1, EIF3E, COX7B, SEC61G, NACA, SAMSN1, USMG5, PSMA4, GAPT, CXCL10, RPL21, MTRNR2L8, MTRNR2L2, MTRNR2L9, MIR2861, GZMA, LAMP1, GZMH, PRF1, BAMB, FCGR3A, KLRK1, GZMK, and GZMM.

Various objects, features, aspects and advantages of the inventive subject matter will become more apparent from the following detailed description of preferred embodiments, along with the accompanying drawing in which like numerals represent like components.

DETAILED DESCRIPTION

Figure 1:
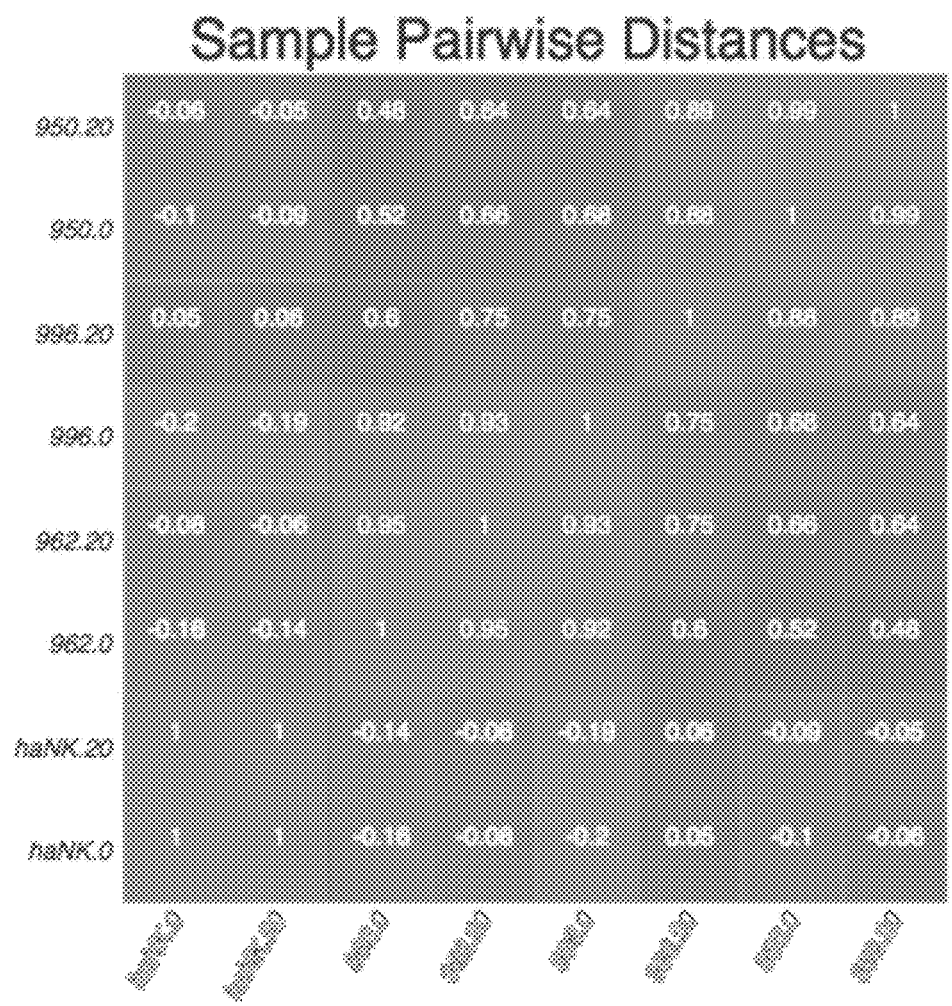
FIG. 1 is a graph depicting pairwise relative distances between exemplary donor NK cells (962, 996, 950) under normoxic (0.20) and hypoxic (0.0) conditions and haNK cells under normoxic (0.20) and hypoxic (0.0) conditions.

The inventors have discovered that NK cell based cancer treatment can be suitable for a tumor even where the tumor has a hypoxic tumor microenvironment, provided that the NK cells are determined to be active, or that such NK cells are treated to regain or retain activity in the hypoxic tumor microenvironment. Most preferably, determination of a hypoxic tumor microenvironment is on the basis of a specific set of hypoxia-related genes in NK cells as is shown in more detail below. As will be readily appreciated, knowledge of hypoxic conditions in the tumor and restored/retained NK activity in hypoxic conditions is advantageous not only for NK cell-based treatment, but also beneficial where a patient is given a drug that leads to hypoxic conditions in the tumor (e.g., bevacizumab).

The inventors' discovery is at least in part based on the unexpected observation that, contrary to conventional wisdom, certain hypoxia related genes are down-regulated (under-expressed) in NK cells at hypoxic (and more typically severely hypoxic, such as <0.5% $O_2$) conditions. Under previously known experimental conditions, hypoxia typically induced in many tissues production of HIF-1α, which is a transcription factor for genes that are up-regulated under control of the hypoxia-inducible promoter (e.g., HRE, hypoxia response element). In contrast, HIF-1α, and selected genes regulated by HIF-1α, were found to be strongly under-expressed in NK cells as compared to normoxic (20% $O_2$) conditions and as such provide a specific indicator as to the presence (and possibly severity) of hypoxia in the tumor microenvironment.

Therefore, upon detection of hypoxia in the tumor microenvironment, a subject with such tumor can be treated with NK cells shown to be unaffected by hypoxia with respect to ADCC (antibody dependent cytotoxicity) and cytotoxic cell killing (typically granzyme and granulysin mediated), or can be treated with NK cells that were preconditioned with IL2 to restore ADCC and cytotoxic cell killing, and/or can be treated with an agent that will revert under-expression of affected NK cells to expression levels associated with NK cells under normoxic conditions. Viewed from a different perspective, it should therefore be appreciated that NK cell based treatment options that would have otherwise been disregarded due to the presence of a hypoxic tumor microenvironment (e.g., due to downregulation of NKG2D on NK cells, NKG2D ligands on tumor cells, and deactivation of ADCC and cytotoxic cell killing) can now be undertaken. Similarly, where it was heretofore uncertain whether or not a tumor has a hypoxic microenvironment, contemplated systems and methods now allow for relatively simple determination of the hypoxic microenvironment.

In an effort to identify differential gene expression as a function of oxygen in a tissue, the inventors tested several NK cell lines under normoxic (20 vol %) and hypoxic (0 vol %) oxygen conditions and performed various omics analyses. More particularly, the tested cell lines were commercially available haNK cells (NantKwest) and NK cells from three different healthy donors as is further described in more detail below. Unexpectedly, the inventors have discovered that at stringent hypoxic conditions numerous genes were significantly down-regulated (under-expressed) that were associated with hypoxia and/or HIF-1α expression. Notably, HIF-1α expression at very low $O_2$ levels (e.g., equal or less than 2 vol %, or equal or less than 1 vol %, or equal or less than 0.5 vol %, or equal or less than 0.1 vol %) was under-expressed, whereas moderate hypoxic conditions are known to increase expression of HIF-1α and genes under the control of HIF-1α. Such oxygen dependent gene-specific downregulation of expression may indeed explain the fact that NK cells lose ability for ADCC and cytotoxic cell killing.

As is shown in more detail below, under-expressed genes in NK cells under hypoxia conditions included HIF-1α (HIF1A), ARL17B, PYHIN1, RPS24, CD52, RPL34, HSPA8, SLIRP, RPS11, B2M, RPS27, MYL12B, RPL39, RPS3A, PTPRC, NAMPT, CALM2, RGS1, KLRB1USP16, RAB8B, RPL26, RPS15A, CCL2, IFI16, CLEC2B, TANK, HSP90AA1, RPS21, KLRK1, RPS29CXCL8, YPEL5, EVI2B, GLIPR1, MARCH7, KLRF1, EIF3E, COX7B, SEC61G, NACA, SAMSN1, USMG5, PSMA4, GAPT, CXCL10, RPL21, MTRNR2L8, MTRNR2L2, MTRNR2L9, MIR2861, GZMA, LAMP1, GZMH, PRF1, BAMB, FCGR3A, KLRK1, GZMK, and GZMM. Notably, at least some of these genes are known to have functional impact with cytotoxic cell killing NK cells (e.g., granzyme related genes). Therefore, analysis of gene expression in NK cells (e.g., via RNAseq, quantitative rtPCR, quantitative proteomics, etc.) of one or more of the genes presented herein will allow a rapid assessment of the presence of a hypoxic tumor microenvironment.

The inventors further unexpectedly discovered that certain NK cells did not exhibit under-expression of the above specified (and certain other, see below) genes, but that these NK cells even exhibited moderate over-expression of these genes (as compared to normoxic conditions) as is shown in more detail below. Notably, these cells did also not have reduced killing activity (ADCC and cytotoxic killing) under hypoxic conditions. For example, such NK cells that were not affected by hypoxia included haNK cells (genetically modified NK92 cells expressing a high affinity variant of CD16 and intracellular IL2, commercially available as haNK cells from NantKwest, 9920 Jefferson Blvd, Culver City, Calif. 90232). Therefore, it should be noted that haNK cells are especially suitable for treatment of a tumor where the tumor was demonstrated to have a hypoxic microenvironment.

In this context, it should be appreciated that such contemplated tests and knowledge of cytotoxic activity under hypoxic conditions is also useful for treatment of a patient with a drug that interferes with tumor neovascularization, which may lead to hypoxic conditions in the tumor microenvironment. For example, it is known that bevacizumab renders a tumor microenvironment hypoxic, which was deemed undesirable as such conditions tend to inhibit NK cell killing. Conversely, where bevacizumab was administered, use of NK cell treatment was typically not advised. Use of, or generation of NK cells that can resist inhibition of ADCC and/or cytotoxic cell killing under hypoxic conditions can therefore greatly enhance the use of drugs that may generate hypoxic conditions. Table 1 below exemplifies therapeutic and other agents known to interfere with tumor neovascularization.

TABLE 1

| Inhibitors | Mechanism |
| --- | --- |
| bevacizumab (Avastin) | VEGF |
| itraconazole | inhibits VEGFR phosphorylation, glycosylation, mTOR signaling, endothelial cell proliferation, cell migration, lumen formation, and tumor associated angiogenesis. |
| carboxyamidotriazole | inhibit cell proliferation and cell migration of endothelial cells |
| TNP-470 (an analog of fumagillin) | |
| CM101 | activate immune system |
| IFN-α | downregulate angiogenesis stimulators and inhibit cell migration of endothelial cells |
| IL-12 | stimulate angiogenesis inhibitor formation |
| platelet factor-4 | inhibits binding of angiogenesis stimulators |
| suramin | |
| SU5416 | |
| thrombospondin | |
| VEGFR antagonists | |
| angiostatic steroids + heparin | inhibit basement membrane degradation |
| Cartilage-Derived Angiogenesis Inhibitory Factor | |
| matrix metalloproteinase inhibitors | |
| angiostatin | inhibit cell proliferation and induce apoptosis of endothelial cells |
| endostatin | inhibit cell migration, cell proliferation and survival of endothelial cells |
| 2-methoxyestradiol | inhibit cell proliferation and cell migration and induce apoptosis of endothelial cells |
| tecogalan | inhibit cell proliferation of endothelial cells |
| tetrathiomolybdate | copper chelation which inhibits blood vessel growth |
| thalidomide | inhibit cell proliferation of endothelial cells |
| thrombospondin | inhibit cell migration, cell proliferation, cell adhesion and survival of endothelial cells |
| prolactin | VEGF |
| $\alpha_v\beta_3$ inhibitors | induce apoptosis of endothelial cells |
| linomide | inhibit cell migration of endothelial cells |
| tasquinimod | Unknown |
| ranibizumab | VEGF |

Based on the transcriptional differences between healthy donor NK cells and haNK cells and further observations (see below), the inventors therefore also contemplate that NK cells may be pre-conditioned before administration with one or more agents that render the so treated NK cells less sensitive or even insensitive to hypoxia. For example, and among other suitable options it is contemplated that the NK cells with reduced expression may be isolated and re-activated in vitro with IL-2 or IL2 analog to thereby increase expression of the down-regulated genes. Similarly, the cells may also be isolated and re-activated in vitro with a STAT3 inhibitor (e.g., using peptide and non-peptide Inhibitors targeting the STAT3 SH2 domain, inhibitors targeting the DNA-binding domain of STAT3, inhibitors targeting STAT3 N-terminal domain, etc.) to thereby increase expression of the down-regulated genes. In further alternative aspects, NK cells may also be transfected with a recombinant nucleic acid that encodes STAT3, IL2, or an IL2 analog, which may be permanently or transiently intracellularly expressed (i.e., not secreted) in the transfected cell. Once pre-conditioned, restoration of the under-expressed gene expression to normal levels can be performed using quantitative analysis of expression of the genes. The so treated cells can then be reintroduced to the patient. Alternatively, haNK cells may be administered to as patient diagnosed with a hypoxic tumor microenvironment.

With respect to suitable NK cells for pre-conditioning it is generally contemplated that the NK cells may be autologous NK cells from the patient, and such autologous NK cells may be isolated from whole blood, or cultivated from precursor or stem cells using methods known in the art.

Moreover, it should be appreciated that the NK cells need not be autologous, but may also be allogenic, or heterologous NK cells. However, in particularly preferred aspects of the inventive subject matter, the NK cells are genetically engineered to achieve one or more desirable traits, are NK92 cells, or derivatives of NK92 cells. For example, in one particularly preferred aspect of the inventive subject matter, the genetically engineered NK cell is a NK92 derivative that is modified to have reduced or abolished expression of at least one killer cell immunoglobulin-like receptor (KIR), which will render such cells constitutively activated (via lack of or reduced inhibition).

NK92 cells exhibit an unusual receptor expression profile, expressing a relatively large number of activating (e.g., NKp30, NKp46, 2B4, NKGD, CD28) receptors. Conversely, NK92 cells also express few inhibitory receptors (e.g., NKGA/B, low levels of KIR2DL4, ILT-2), and lack most of the killer inhibitory receptors (KIRs) clonally expressed on normal NK cells. In addition, NK92 expresses relatively high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. Moreover, NK92 cells also express other molecules implicated immune effector cell regulation (CD80, CD86, CD40L, TRANCE) whose relevance in NK killing is unclear.

Moreover, suitable NK cells may have one or more modified MR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated MR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells ('activated natural killer cells).

In another preferred aspect of the inventive subject matter, the genetically engineered NK cell may also be an NK92 derivative that is modified to express the high-affinity Fcγ receptor (CD16). Sequences for high-affinity variants of the Fcγ receptor are well known in the art (see e.g., Blood 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells ('high-affinity natural killer cells).

In yet a further aspect of the inventive subject matter, the genetically engineered NK cell may also be genetically engineered to express a chimeric T-cell receptor. In especially preferred aspects, the chimeric T-cell receptor will have a scFv portion or other ectodomain with binding specificity against a tumor associated antigen, a tumor specific antigen, and a cancer neoepitope. As noted before, there are numerous manners of genetically engineering an NK cell to express such chimeric T-cell receptor, and all manners are deemed suitable for use herein. Alternatively, such cells may also be commercially obtained from NantKwest as taNK cells ('target-activated natural killer cells').

Therefore, and viewed from a different perspective, all NK cells contemplated herein may also be genetically modified to express non-secreted IL-2 (e.g., retained in the ER compartment). Where NK cells are pre-treated with IL-2 and/or IL-12 it is generally contemplated that physiological or common in vitro concentrations well known in the art are employed. For example, suitable concentrations of IL-2 and/or IL-12 include 1-100 U/ml, 100-1,000 U/ml, or 10-10,000 U/ml, and even higher. On the other hand, IL-2 and/or IL-12 may also be expressed form a recombinant nucleic acid within the cell, and the recombinant protein may be secreted, or more typically, retained within the cell.

In yet another aspect of the inventive subject matter, thusly modified NK cells may be used in a pharmaceutical composition, typically formulated as a sterile injectable composition with between $10^4$-$10^{11}$ cells, and more typically $10^5$-$10^9$ cells per dosage unit. However, alternative formulations are also deemed suitable for use herein, and all known routes and modes of administration are contemplated herein. As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection into the tumor, infusion, oral delivery, topical delivery, etc.).

Most typically, contemplated treatments will also include (metronomic) low dose chemotherapy/radiation to induce NKG2D ligands on the tumor tissue. For example, preferred treatments include low dose chemotherapy and/or low dose radiation therapy, typically performed at dosages that are equal or less than 50%, equal or less than 30%, equal or less than 20%, or equal or less than 10% of the maximum tolerated dose. Moreover, such low dose treatment will preferably be performed in a metronomic fashion, for example, on alternating days, or every third day, or once weekly for several weeks, etc.

Therefore, the inventors contemplate various methods of testing NK cells of a patient diagnosed with a tumor, as well as methods of diagnosing and treating a tumor having a hypoxic tumor microenvironment, and methods of treating a tumor having a hypoxic tumor microenvironment. As noted above, presence of the hypoxia in the tumor microenvironment can be established by determination of the expression level of selected genes in the NK cells of a patient (typically isolated from blood). Under-expression of at least one, or at least two, or at least five, or at least 10 genes relative to normoxic conditions is indicative of hypoxia. Once detected, counter measured may be administered, and especially preferred compounds or compositions include haNK cells, and/or conditioned NK cells (e.g., with IL-2 or STATE3 inhibitor) having reduced inhibition of cell killing in hypoxic conditions as compared to the same NK cell without conditioning. Alternatively, the STAT5 inhibitor may also be directly administered to the patient.

EXAMPLES

Frozen RNA extracted from 2 donor populations of NK lines that were cultured under two conditions (normoxic, 20% $O_2$; and hypoxic, 0% $O_2$) and a haNK line (commercially obtained from NantKwest) were used for the downstream analyses. RNA-seq libraries were prepared using the KAPA Stranded RNA-Seq Kit with RiboErase (Kapa Biosystems, Wilmington, Mass.) and sequenced to a target depth of 200M reads on the Illumina HiSeq platform (Illumina, San Diego, Calif.). Samples were aligned to RefSeq build 73 transcriptome using Bowtie2 v2.2.6 and quantified using RSEM v1.2.25 to transcripts per million (TPM). Downstream analysis was done in Python v2.7.6 using numpy v1.11.1, scipy v0.17.1, and pandas v0.18.1.

An overall comparison of expression levels was performed on all cell lines under both normoxic and hypoxic conditions, and FIG. 1 depicts exemplary results. Here, the pairwise Pearson correlations of RNA $\log_2$-TPM data from pairs of patient donor samples showed that inter-patient variability was much higher than with other sets of donor NK lines and haNK cells (average intra-sample r=0.968, average inter-sample r=0.857). Despite the difference between samples, when compared between the 0% and 20% oxygen conditions, the patient donor NK lines were more like each other than the haNK line (avg haNK vs patient r=−0.00317, average patient r=0.575). Indeed, it was observed that the haNK cell line remained substantially unaffected in the pairwise correlation comparing the normoxic and hypoxic conditions, while the donor NK cell populations all exhibited strong differences between the normoxic and hypoxic conditions.

Figure 2:
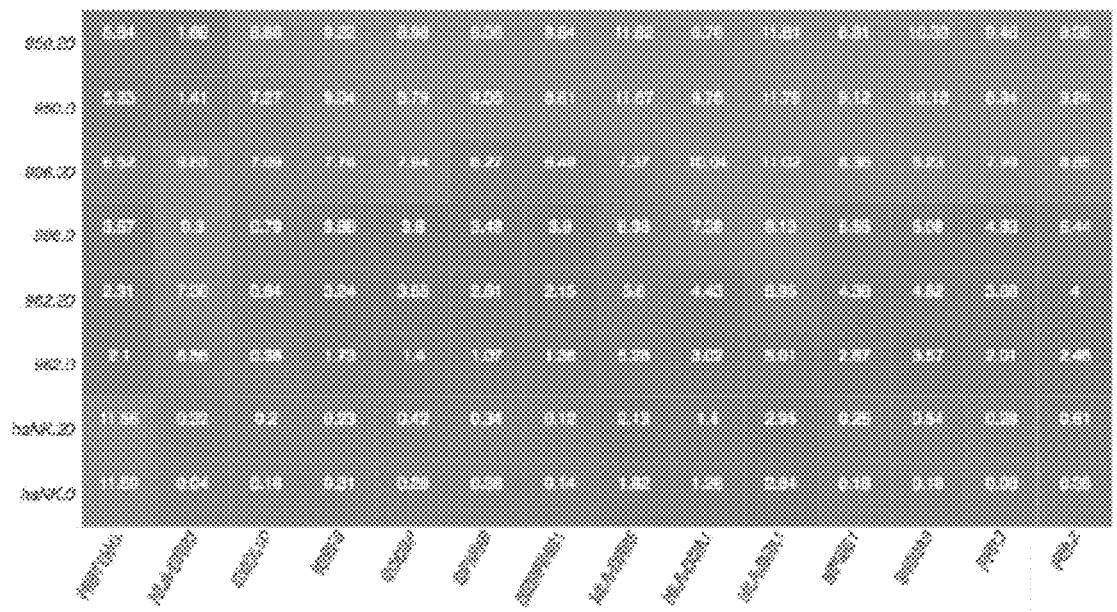
FIG. 2 is a graph depicting the most variable genes across all cells of FIG. 1.
Figure 2:
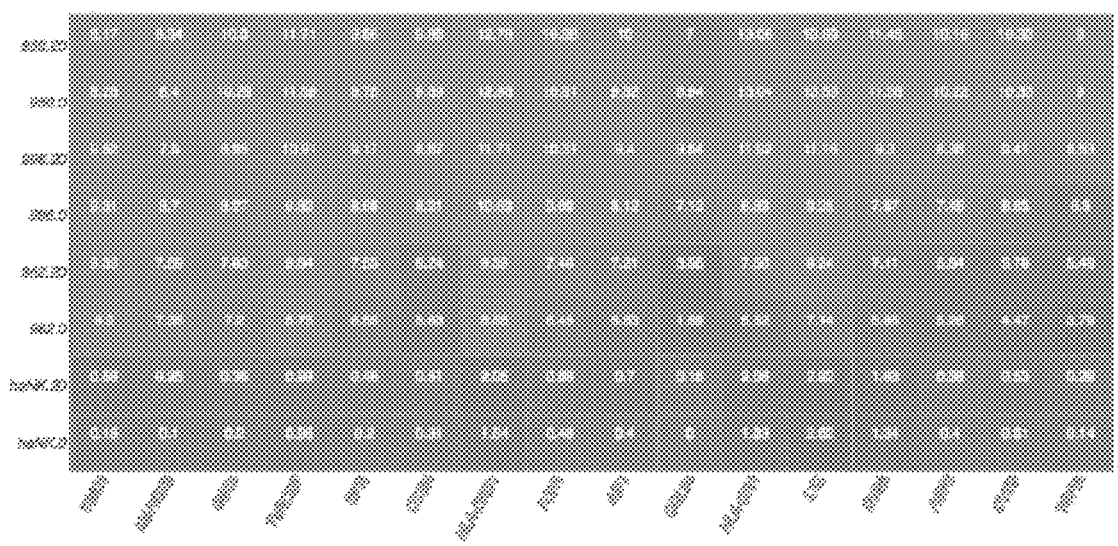

In order to identify specific hypoxic transcriptional changes relative to the normal NK donor lines, the NK TPMs were normalized to the difference in $log_2$-TPMs of the normal donor cells. Z-scores for each gene were calculated based on the overall distribution of centered TPM ratios ($log_2$ difference) in the normal samples, which resulted in a mean of 0 and a standard deviation of 0.453. FIG. 2 illustrates exemplary results for most variably expressed genes between both conditions. Many of the top transcripts identified showed significantly decreased expression in the donor NK lines while remaining active in the haNK lines, indicating that the haNK cells continue to replicate despite the hypoxic conditions. Beyond cell-cycle, transcripts related to HIF1A, STAT1 and STAT2 appeared to be some of the most differentially expressed genes similarly unaffected by hypoxia but significantly decreased in the donor NK cells. Previously published reports (PMID: 22615451) have shown continued expression of the STAT1 pathway as being critical to resistance to cytotoxic factors.

Figure 3:
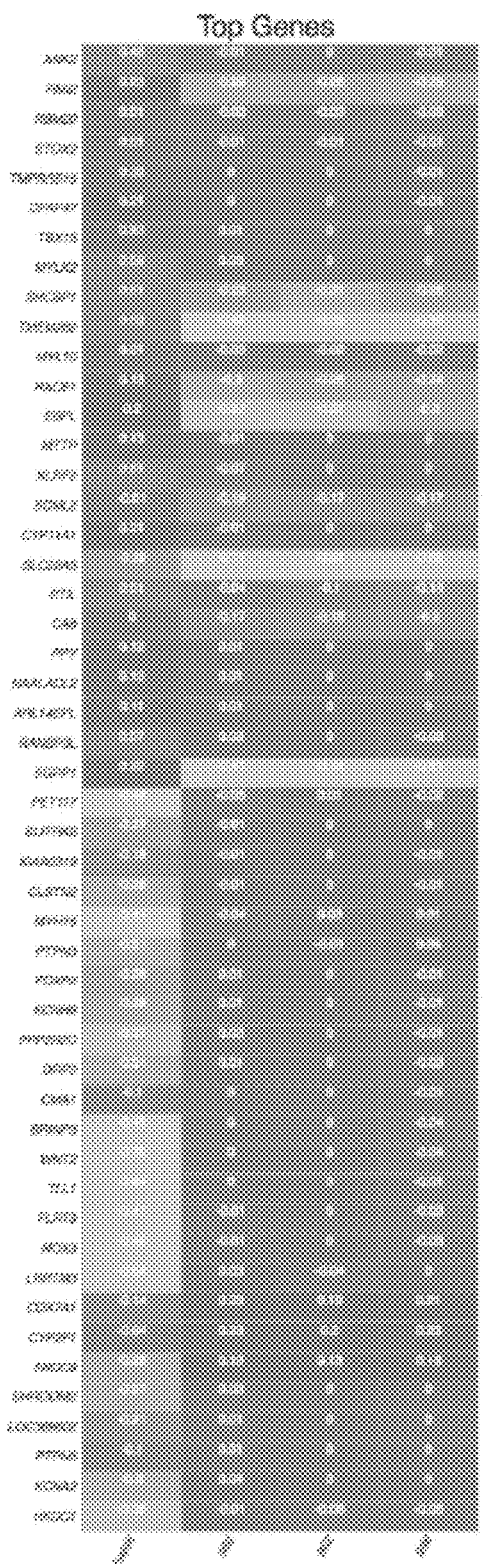
FIG. 3 is a graph depicting top changes in gene expression between normoxic and hypoxic conditions for all cells of FIG. 1.
Figure 4:
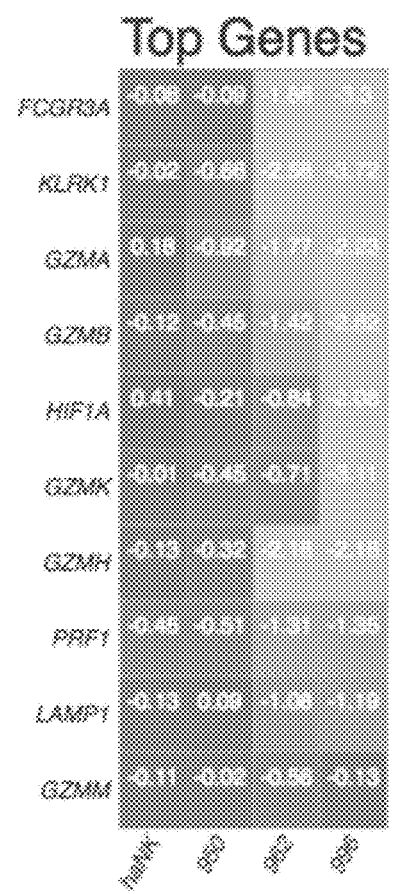
FIG. 4 is a graph depicting an exemplary contemplated hypoxia-related gene set most likely to have changed between conditions.
Figure 5:
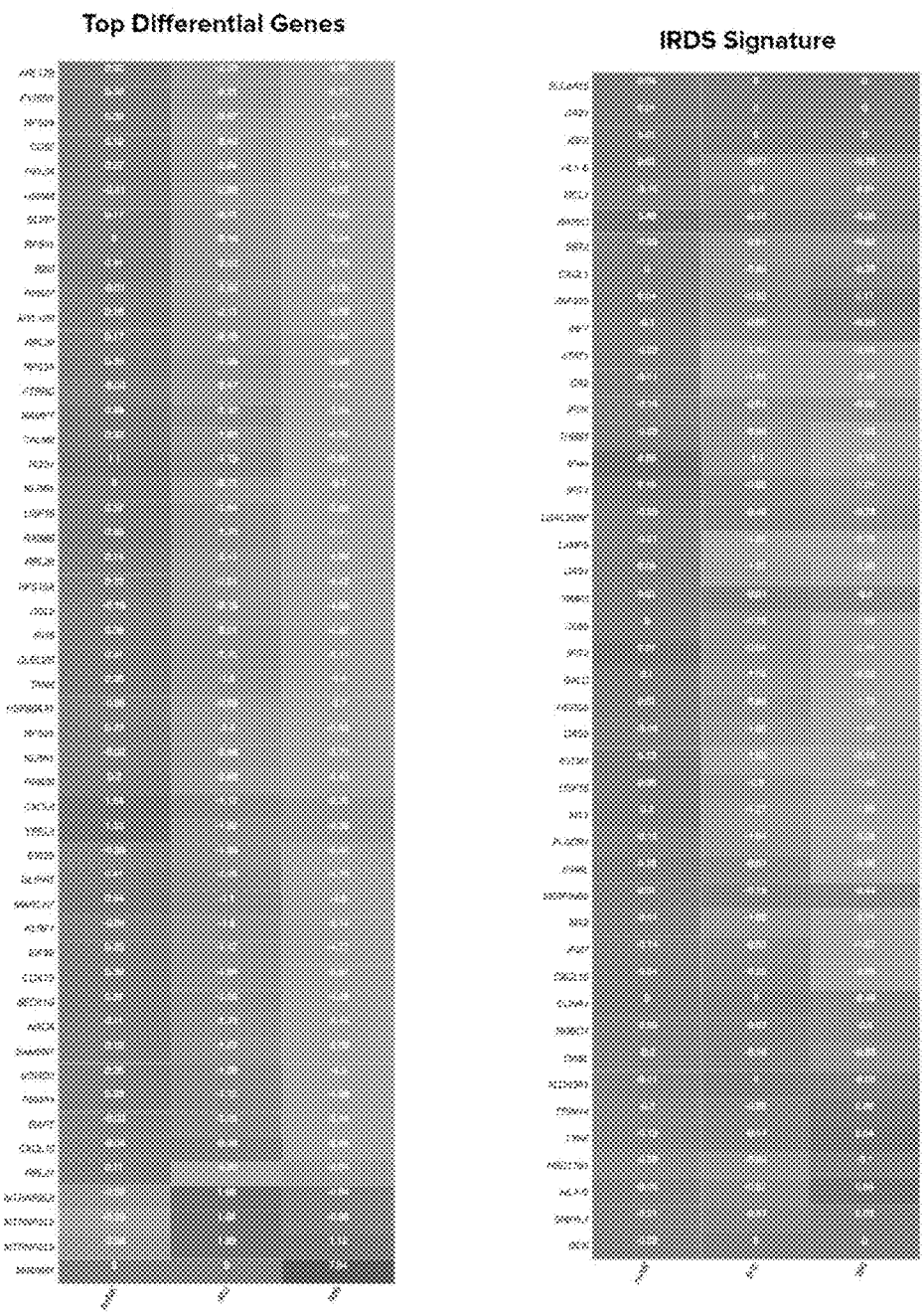
FIG. 5 is a graph depicting exemplary transcriptional differences in haNK cell gene expression relative to donor NK cells for the top differentially expressed genes and the genes in an IFN-related DNA damage resistance signature (IRDS) signature.
Figure 6:
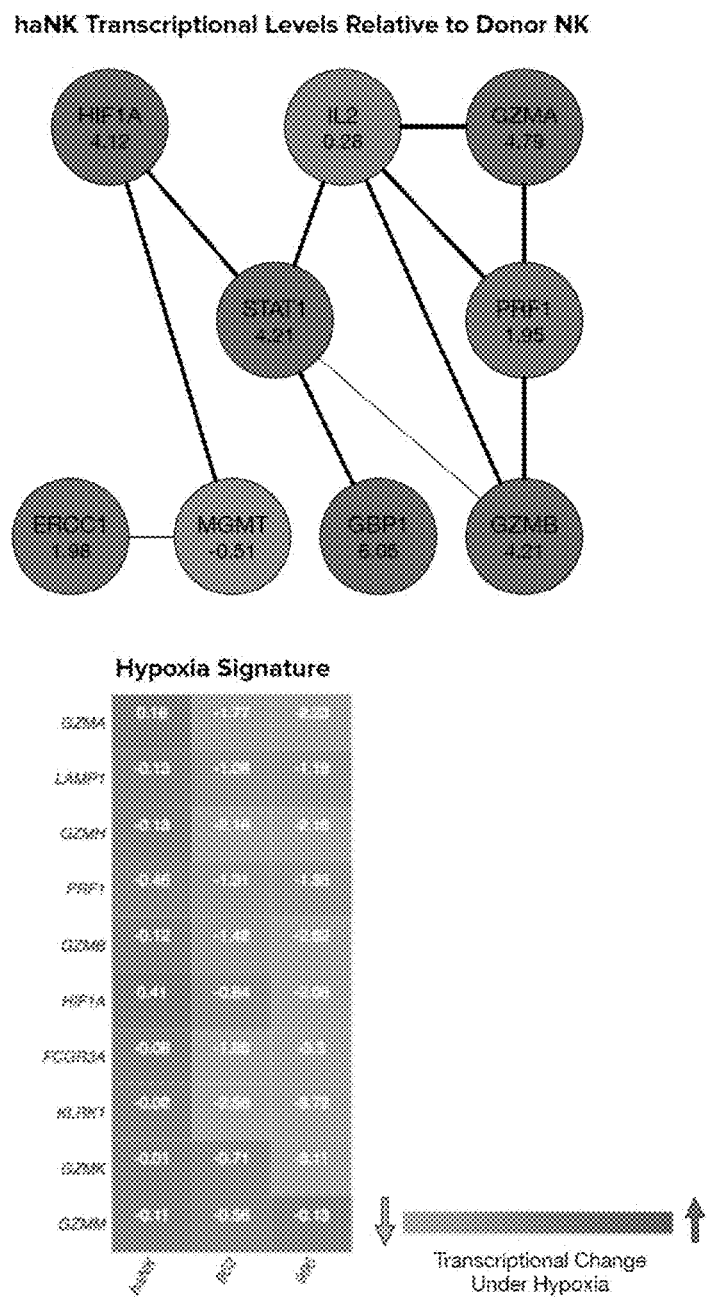
FIG. 6 is a graph depicting exemplary transcriptional differences in haNK cell gene expression relative to donor NK cells with respect to a hypoxia signature and selected proteins.

FIG. 3 shows expression level differences ($log_2$ fold differences) of selected genes between the normoxic and hypoxic conditions for various cell lines. As can be readily seen from FIG. 3, the expression levels for the selected genes were relatively unaffected, and in some cases even increased, while the expression differences for the three healthy donor populations (950, 962, 966) were mostly and significantly negative. FIG. 4 shows a subset of substantial differential expression levels of markers predominantly relevant for NK cells (e.g., HIF1A, and granzyme genes GZMA, GZMB, GZMH, GZMK, GZMM). A further data comparison of differential expression ($log_2$ fold differences) for selected genes is shown in FIG. 5, by top differences (left panel) and IFN-related DNA damage resistance signature (IRDS, right panel). Once more, the differences between haNK cells and donor cells were substantial, with most of the differentially expressed genes down-regulated in the donor cell lines under hypoxic conditions. FIG. 6 exemplarily illustrates a subnetwork related to HIF-1 and STAT1 with corresponding z-scores showing the relative significance of expression of genes in haNK cells versus donor cells.

Figure 7:
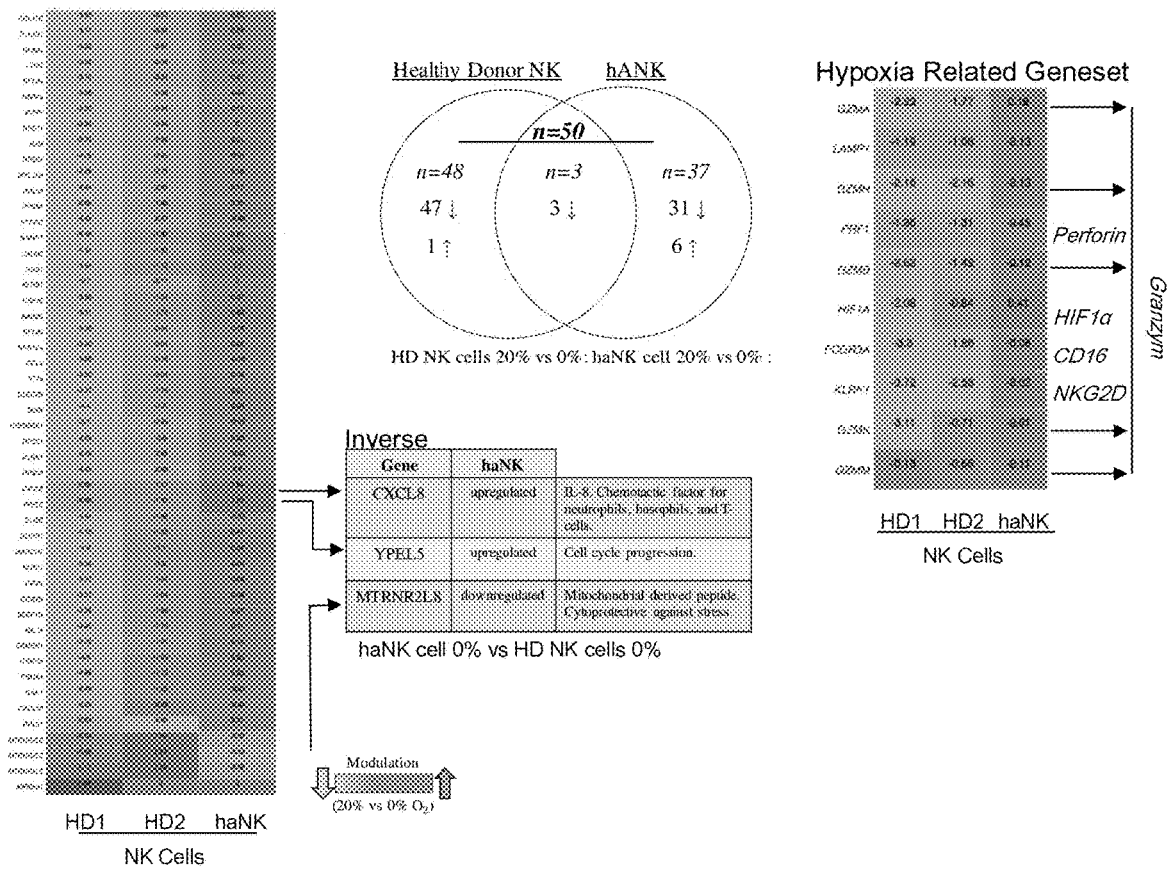
FIG. 7 is another exemplary graph depicting differences in gene expression for a hypoxia related gene set for the cells of FIG. 1.

When analyzing top differential genes between donor cells and haNK cells as is shown in FIG. 7, it became apparent that upregulated genes in haNK cells under hypoxia were related to NK cell function, while up-regulated genes in donor cells were related to stress reactions. Likewise, when analyzing a hypoxia geneset, it was observed that granzyme, perforin, and HIF1A genes were strongly up-regulated in haNK cells and significantly under-expressed in donor cells.

Figure 8:
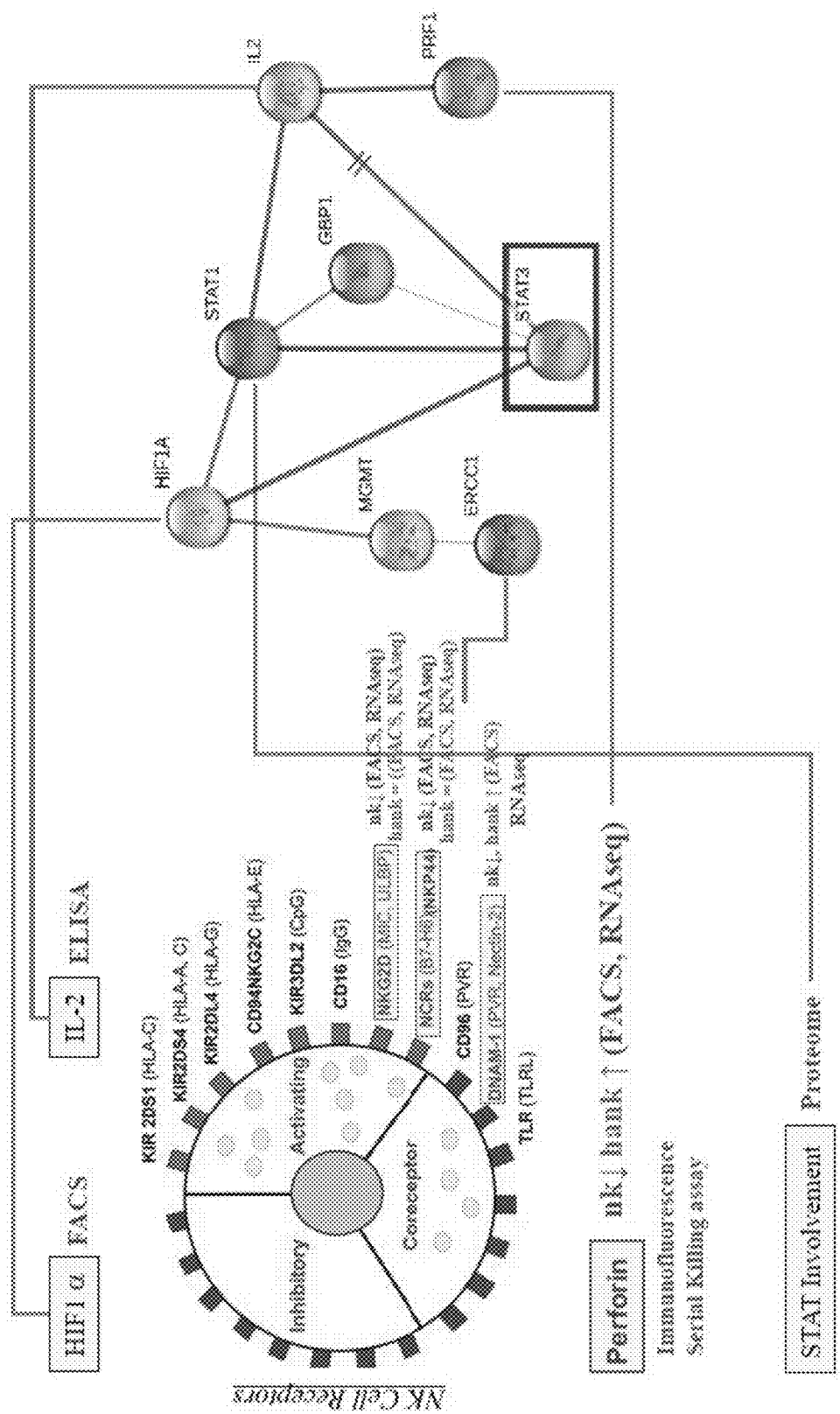
FIG. 8 is an exemplary graph depicting contemplated regulatory effects associated with NK cell hypoxia.

FIG. 8 schematically illustrates a regulatory subnetwork affecting HIF1A and IL2, with STAT3 a potential master regulator for the factors shown in FIG. 8. Thus, as STAT3 is involved in the regulation of various genes with changes observed above, the inventors contemplate that STAT3 inhibitors could potentially reverse the hypoxia dependent under-expression of the genes listed above.

Consequently, it should be appreciated that a test quantifying expression levels of the genes in NK cells of a patient may be useful in determination whether or not a patient's own NK cells will retain activity under hypoxic conditions, or whether a patient will benefit of administration of haNK cells. Alternatively, patient NK cells may also be pre-treated with IL-2, IL-12, and/or a STAT3 inhibitor to induce a greater resistance in the patient's NK cells to inhibition of cytotoxic activity under hypoxic conditions. For example, the inventors noted that NK cell lytic activity can be partially rescued by exogenous IL-2 activation in vitro (e.g., 16 h, 1000 IU/ml). Such treated NK cells retained ADCC capacity at 1% $O_2$.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Moreover, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a tumor in a human patient having a hypoxic tumor microenvironment, the method comprising:
   isolating natural killer (NK) cells from a blood sample taken from the patient;
   quantifying expression of at least one hypoxia-related gene in the isolated NK cells, wherein the hypoxia related gene is HIF-1α, and wherein the NK cells under-express the at least one hypoxia-related gene relative to an expression level of the at least one hypoxia-related gene in an NK cell at normoxic conditions; and administering an effective amount of allogenic NK92 cells expressing a high-affinity variant CD16 (haNK) cells to the patient whose isolated NK cells under-express the at least one hypoxia-related gene.

2. The method of claim 1 wherein the NK cells are isolated using magnetic separation and an antibody specific to NK cells.

3. The method of claim 1 wherein quantifying expression is performed using quantitative rtPCR or RNAseq.

4. The method of claim 1 wherein the at least one hypoxia-related gene is under-expressed by a log 2-fold change of at least 2.0.

* * * * *